(12) United States Patent
Wright

(10) Patent No.: US 6,766,801 B1
(45) Date of Patent: Jul. 27, 2004

(54) INTRA-TRACHEAL AEROSOL DELIVERY SYSTEM AND METHOD OF USING SAME

(75) Inventor: Clifford A. Wright, San Diego, CA (US)

(73) Assignee: Medical Device Group, Inc.

( * ) Notice: Subject to any disclaimer, the term of this patent is extended or adjusted under 35 U.S.C. 154(b) by 0 days.

(21) Appl. No.: 10/431,811

(22) Filed: May 5, 2003

(51) Int. Cl.$^7$ ............................................. A61M 16/00
(52) U.S. Cl. .............................. 128/207.14; 128/200.14
(58) Field of Search ........................ 128/200.14, 200.15, 128/200.18, 200.26, 203.12, 203.23, 203.24, 207.14, 207.15, 207.18; 239/461–470, 490–492

(56) References Cited

U.S. PATENT DOCUMENTS

| | | | | |
|---|---|---|---|---|
| 4,669,463 A | * | 6/1987 | McConnell | 128/207.14 |
| 5,025,806 A | * | 6/1991 | Palmer et al. | 128/203.12 |
| 5,031,613 A | * | 7/1991 | Smith et al. | 128/207.14 |
| 5,078,131 A | * | 1/1992 | Foley | 128/203.15 |
| 5,438,982 A | * | 8/1995 | MacIntyre | 128/207.14 |
| 5,605,147 A | * | 2/1997 | Truthan | 128/203.12 |
| 5,803,078 A | * | 9/1998 | Brauner | 128/207.14 |
| 6,009,868 A | * | 1/2000 | Nilson | 128/200.18 |
| 6,079,413 A | * | 6/2000 | Baran | 128/207.14 |
| 6,237,597 B1 | * | 5/2001 | Kovac | 128/207.14 |
| 6,526,976 B1 | * | 3/2003 | Baran | 128/207.14 |
| 6,575,944 B1 | * | 6/2003 | McNary et al. | 604/264 |
| 2003/0172934 A1 | * | 9/2003 | Croll et al. | 128/207.14 |

OTHER PUBLICATIONS

MADett Pulmonary Drug Delivery at http://www.wolfetory.com.

* cited by examiner

*Primary Examiner*—Teena Kay Mitchell

(57) ABSTRACT

An aerosol delivery system includes an endotracheal tube with a sub-port having a sufficient diameter to permit the passage of a sub-port tube therethrough. The sub-port tube passes within the interior of the endotracheal tube via the sub-port and includes a passageway that terminates in an atomizer nozzle at the distal end of the sub-port tube. The atomizer nozzle and the endotracheal tube are integrally connected to one another at a distal end base outlet of the endotracheal tube. A delivery conduit having an atomizer connector at its distal end is adapted to be connected to a canister for delivering fluid under pressure. The delivery conduit has a sufficient length to pass within the sub-port tube to lockingly engage the atomizer nozzle atomizer, whereby fluid delivered under pressure from the canister flows to the atomizer nozzle causing an aerosol mist to be dispensed outwardly from the base outlet of the endotracheal tube.

16 Claims, 2 Drawing Sheets

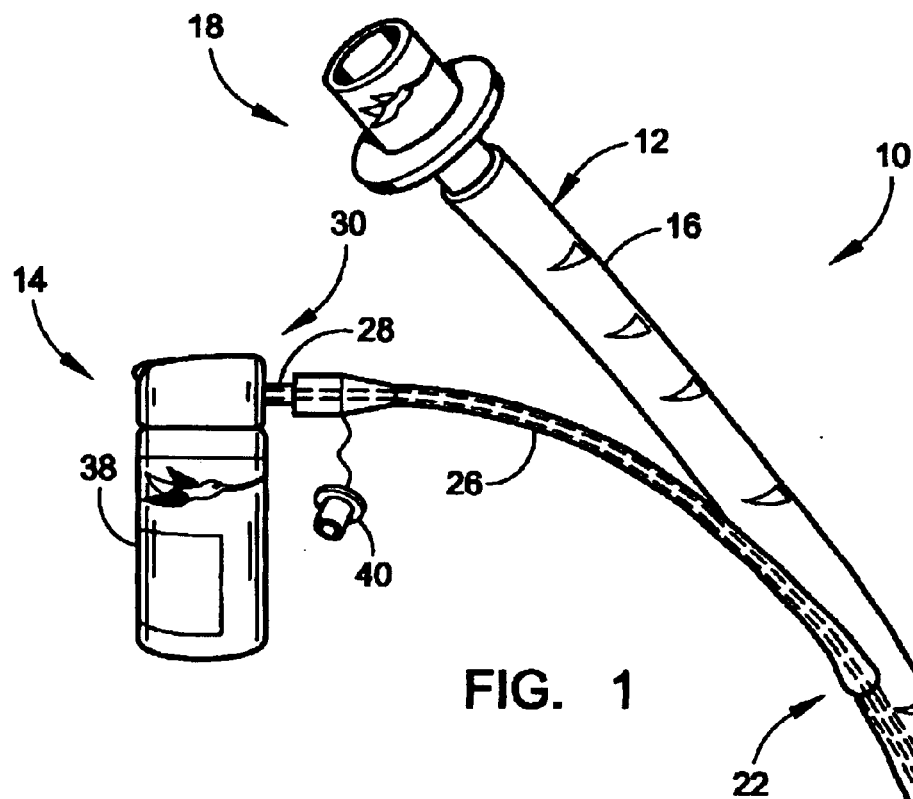
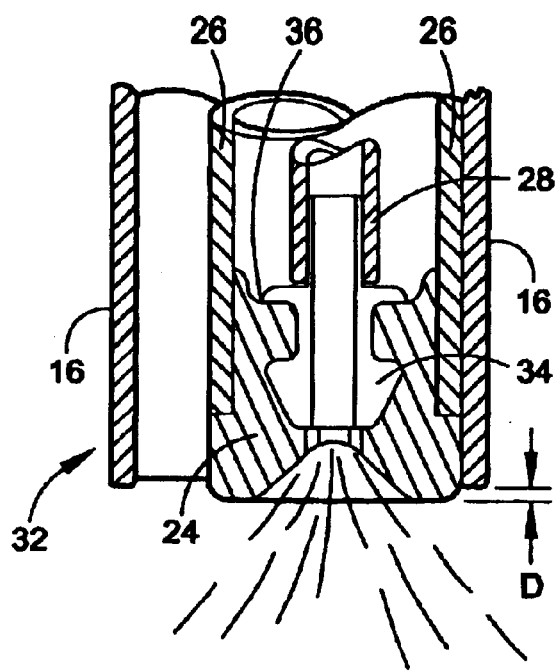
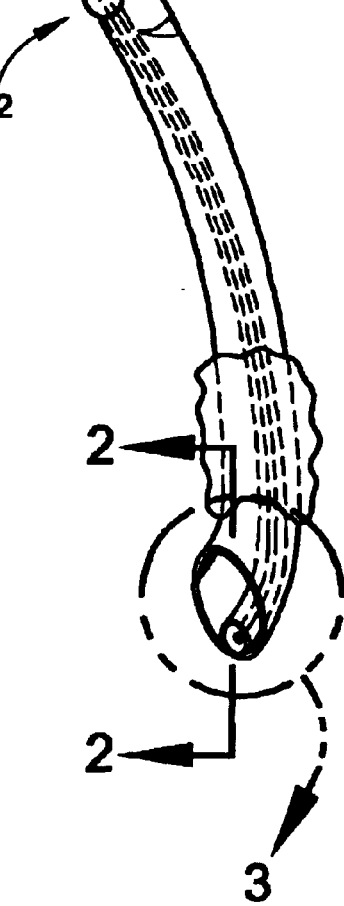
FIG. 1
FIG. 2

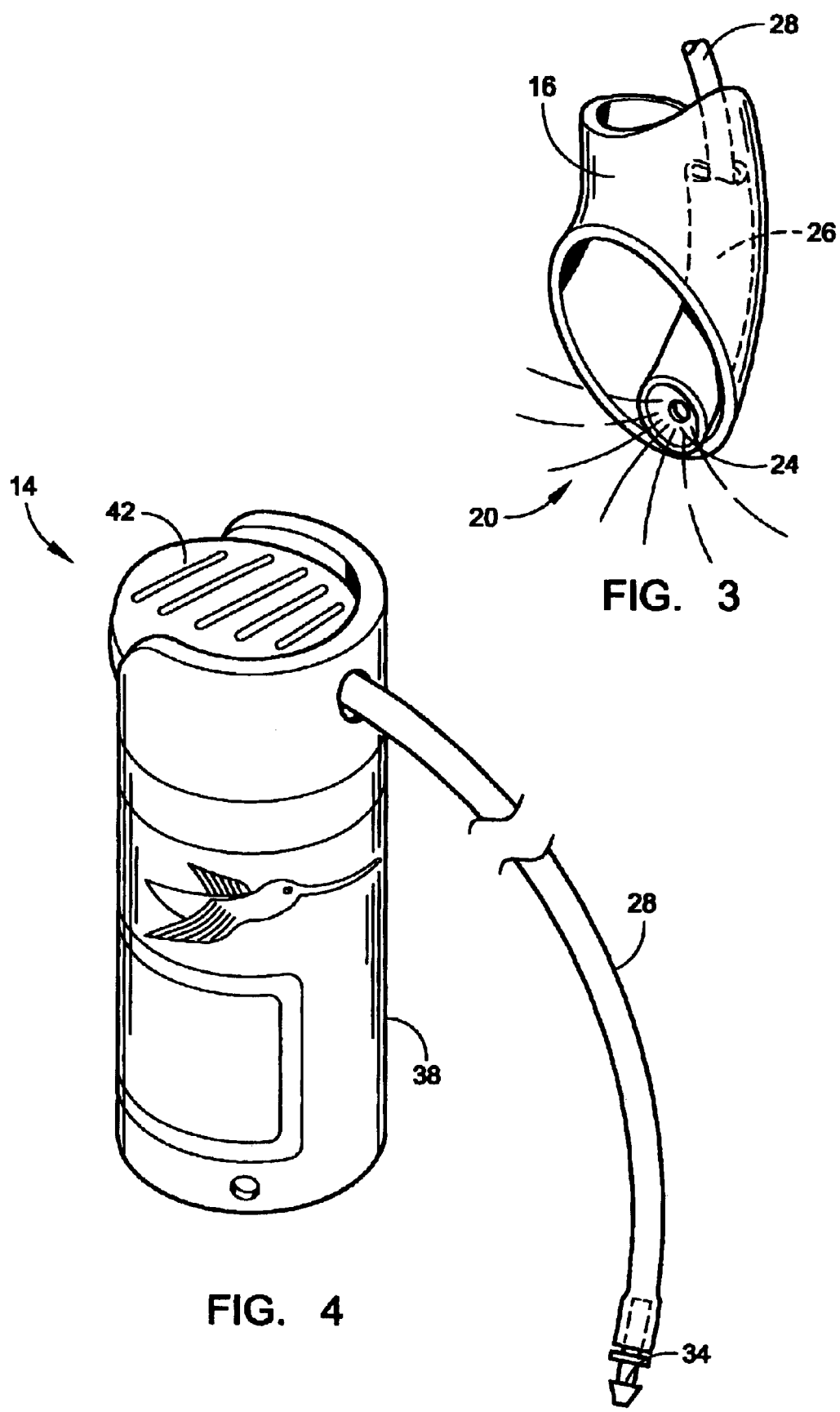

INTRA-TRACHEAL AEROSOL DELIVERY SYSTEM AND METHOD OF USING SAME

FIELD OF THE INVENTION

The present invention relates to a device for facilitating medicating a patient and more particular to a patient care device that facilitates delivering a therapeutic aerosol by endotracheal means deep into the lungs of a patient.

BACKGROUND

Delivery of medications into the lungs of a patient is generally accomplished in two different ways, e.g. either or by directly delivering a liquid bolus of the drug or by insertion of a delivery catheter through the larynx or through an artificial airway such as endotracheal or by a tracheostomy tube. However, the presence of an endotracheal tube poses a particular problem since the endotracheal tube operates as a significant site of impaction of an externally generated therapeutic aerosol. Moreover, some endotracheal tube materials may promote aerosol rainout while the presence of an electrostatic charge on the tube itself can also reduce the ability of the aerosol to pass through the tube. Therefore, it would be highly desirable to have a new and improved method and apparatus for delivering a therapeutic aerosol by endotracheal means deep into the lungs of a patent.

SUMMARY OF THE INVENTION

An aerosol delivery system includes an endotracheal tube with a sub-port having a sufficient diameter to permit the passage of a sub-port tube therethrough. The sub-port tube passes within the interior of the endotracheal tube via the sub-port and includes a passageway that terminates in an atomizer nozzle at the distal end of the sub-port tube. The atomizer nozzle and the endotracheal tube are integrally connected to one another at a distal end base outlet of the endotracheal tube. A delivery conduit having an atomizer connector at its distal end is adapted to be connected to a canister for delivering fluid under pressure. The delivery conduit has a sufficient length to pass within the sub-port tube to lockingly engage the atomizer nozzle atomizer, whereby fluid delivered under pressure from the canister flows to the atomizer nozzle causing an aerosol mist to be dispensed outwardly from the base outlet of the endotracheal tube.

BRIEF DESCRIPTION OF THE DRAWINGS

The above mentioned features and steps of the invention and the manner of attaining them will become apparent, and the invention itself will be best understood by reference to the following description of the embodiments of the invention in conjunction with the accompanying drawings wherein:

FIG. 1 is a perspective view of a intra-tracheal aerosol delivery system, which is constructed in accordance with the present invention;

FIG. 2 is an enlarged cross sectional view of a patient care device taken along lines 2–2 of FIG. 1;

FIG. 3 is an enlarged fragmentary view of a distal end portion of the patient care device of FIG. 1;

FIG. 4 is a perspective view of a medication delivery device for use with the patient care device of FIG. 1;

DETAILED DESCRIPTION OF THE PREFERRED EMBODIMENTS

Referring now to the drawings and more particularly to FIGS. 1–4 there is illustrated an intra-tracheal aerosol delivery system 10, which is constructed in accordance with the preferred embodiment of the present invention. The intra-tracheal aerosol delivery system 10 is designed to maximize lower respiratory tract deposition of aerosol particles generated by a meter dose inhaler. As will be explained hereinafter in greater detail, the novel method of delivering an aerosol fluid medication to the distal end portion of a endotracheal tube optimizes particle size for distal airway penetration, as well as reduces local mucosal impact and irritation.

Considering now the intra-tracheal aerosol delivery system 10 in greater detail with reference to FIG. 1, the system 10 generally includes a patient care device 12 and a medication delivery device 14. The patient care device 12 facilitates ventilating a patient (not shown) while the medication delivery device 14 facilitates medicating a patient. The patient care device 12 and the medication delivery device 14 cooperate together to optimize aerosol particle size for distal airway penetration, providing an improved and more efficient method of aerosol delivery in mechanically ventilated patients.

Considering now the patient care device 12 in greater detail with reference to FIG. 1, the patient care device 12 generally includes a curved endotracheal tube 16 having a proximal end opening 18, a distal end opening 20 and a sub-port opening 22. An atomizer nozzle 24 is molded to the distal end of the endotracheal tube 16 and extends slightly out from the distal end opening 20 to allow the delivery of a spray mist beyond the distal end of the endotracheal tube 16. In short, there is no drug waste running down the interior wall of the endotracheal tube 16 thereby allowing a clinician to know exactly how much drug is delivered to the patient. Moreover, the patient care device 12 facilitates atomizing drugs directly into the lungs of a patient without interruption of the ventilating process. The unique and novel method of delivering an aerosol spray mist beyond the tip of the endotracheal tube 16 results in more rapid and higher peak lung levels than nebulized or endotracheally injected medication.

In order to allow medication delivery without interruption of the ventilation process, the patient care device 12 also includes a sub-port tube 26 that is molded between the endotracheal tube 16 and the atomizer nozzle 24 at about the distal end 20 of the endotracheal tube 16. In this regard, the atomizer nozzle 24 extends out from the distal end of the sub-port tube 26 a sufficient distance to permit the nozzle 24 to be molded to the interior wall of the endotracheal tube 16 at about its distal end and to extend beyond the distal end 20 of the endotracheal tube 16 by about a distance D. In the preferred embodiment the present invention the distance D is between about 0.2 centimeters and about 0.0 centimeter. A more preferred distance D is between about 0.1 centimeters and about 0.0 centimeters, while the most preferred distance D is about 0.0 centimeters.

From the foregoing, it should be understood by those skilled in the art, that the nozzle 24 and the sub-port tube 26 are integrally attached to one another and integrally attached to the interior wall of the endotracheal tube 16 at about its distal end 20 to insure that neither the nozzle 24 nor the sub-port tube 26 can invade the lungs or trachea of the patient. This is an important feature of the preferred embodiment of the present invention.

The sub-port tube 26 is integrally attached to the interior wall of the endotracheal tube 16 and exits the endotracheal tube 16 at the sub-port opening 22, where it extends out from the endotracheal tube 16 a sufficient distance to be easily accessed by a clinician for drug delivery purposes and without interfering with the connection between the endotracheal tube 16 and a mechanical ventilator (not shown). In this regard, that portion of the sub-port tube 26 that extends out from the endotracheal tube 20 is between about 10 millimeters in length and about 150 millimeters in length. A more preferred length is between about 50 millimeters and about 140 millimeters, while the most preferred length is about 120 millimeters. The exiting of the sub-port tube 26 through the sub-port opening 22 and not the proximal end opening 18 of the endotracheal tube16 is an important feature of the preferred embodiment of the present invention as this facilitates drug delivery without interrupting the ventilation process. In short, a clinician is able to oxygenate, ventilate and medicate with the aerosol delivery system 10.

Considering now the medication delivery device 14 in greater detail with reference to FIGS. 1–4, the medication delivery device 14 generally includes an elongated delivery conduit 28 having a proximal end opening 30 and a distal end opening 32. A nozzle or atomizer connector 34 is disposed in the distal end opening 32 of the delivery conduit 28 and extends out therefrom a sufficient distance to be received and lockingly engage a seat 36 disposed at the proximal end of the nozzle 24. In this regard, when the atomizer connector 34 is received within the seat 36 a fluid tight seal is formed. The seal is an important feature of the preferred embodiment of the present invention as it allows fluid under pressure to be delivered from a canister 38 to the atomizer nozzle 24 without loss of pressure. Thereby a fully pressurized dose of a desired drug can be delivered into the distal airways of the patient. As will be explained hereinafter in greater detail, the seat 36 is constructed to release the atomizer connector 34 when the delivery conduit 28 is pulled by its proximal end to be extracted from the sub-port tube 26.

Considering now the unique and novel method of ventilating and medicating a patient in accordance with the preferred embodiment of the present invention, a clinician inserts the patient care device 12 through either the mouth or nose of a patient so that the distal end of the patient care device 12 is disposed in the trachea of the patient This action also positions the proximal end 18 of the endotracheal tube 16 and the proximal end 30 of the sub-port tube 26 at desired positions for attachment to the mechanical ventilator (not shown) and the medication delivery device 14 respectively. As the method of attaching the endotracheal tube 16 is well known to those skilled in the art, this method will not be described hereinafter in greater detail.

Considering now the method of attaching the medication delivery device 14 to the patient care device 12 in greater detail, the clinician removes a small passageway plug 40 from the proximal end of the sub-port tube 26. Next the clinician attaches the proximal end of the delivery conduit 28 to the canister 38 and then directs the distal end of the delivery conduit 28 into the sub-port tube 26. In this regard, the delivery conduit 28 and its associated nozzle connector 34 each have a sufficiently small diameter to enter the distal end of the sub-port tube 26 and to pass therethrough to cause the nozzle connector 34 to be received within the atomizer nozzle seat 36. In this regard, the delivery conduit 28 is sufficiently stiff to allow the nozzle connector 34 to be pushed into locking engagement with the seat 36 by pushing on the proximal end of the delivery conduit 28.

Once the nozzle connector 34 has been engaged with the seat 36, the clinician attaches the proximal end of the delivery conduit 28 to an outlet of the canister 38. With a fluid passageway having now been established between the canister 38 and the nozzle 24, the clinician actuates a thumb lever 42 disposed on the top of the canister 38 to deliver a precise dosage of medication to the nozzle 24. The nozzle 24 upon receiving the fluid under pressure immediately transforms the fluid into small aerosol particles that emerge from beyond the distal end 20 of the endotracheal tube 16 for delivery into the distal airways of the patient.

After the patient has been medicated, the clinician disengages the proximal end of the delivery conduit 28 from the canister 38 and pulls the free proximal end of the delivery conduit 28 to disengage the nozzle connector 34 from the nozzle 24. The delivery conduit 28 is then extracted from the sub-port tube 26. Once the delivery conduit 28 has been removed from the sub-port tube 26 the proximal end of the sub-port tube 26 is sealed with the air passageway plug 40.

While particular embodiments of the present invention have been disclosed, it is to be understood that various different modifications are possible and are contemplated within the true spirit and scope of the appended claims. There is no intention, therefore, of limitations to the exact abstract or disclosure herein presented.

I claim:

1. A patient care device, comprising:

an endotracheal tube for facilitating ventilating a patient, said tube having a proximal end opening, a distal end opening and a sub-port opening;

a sub-port tube having a proximal end and a distal end, said sub-port tube extending through said sub-port opening and being attached at about its distal end to said endotracheal tube at about its distal end opening;

an atomizer nozzle disposed within said sub-port tube, said atomizer nozzle being partially attached to said sub-port tube at about its distal end and partially attached to said endotracheal tube at about its distal end opening; and said atomizer nozzle having a fluid delivery seat for receiving therein a nozzle connector to facilitate medicating the patient, said nozzle connector being disposed at a distal end of a delivery conduit having a sufficiently small diameter to enter the distal end of said sub-port tube and to pass therethrough to cause said nozzle connector to be received within said fluid delivery seat.

2. A patient care device, comprising:

an endotracheal tube for facilitating ventilating a patient, said tube having a proximal end opening, a distal end opening and a sub-port opening;

a sub-port tube having a proximal end and a distal end, said sub-port tube extending through said sub-port opening and being attached at about its distal end to said endotracheal tube at about its distal end opening;

an atomizer nozzle disposed within said sub-port tube, said atomizer nozzle being partially attached to said sub-port tube at about its distal end and partially attached to said endotracheal tube at about its distal end opening; and said atomizer nozzle having an upstanding nozzle connector to facilitate medicating the patient, said nozzle connector being disposed at a distal end of a delivery conduit having a sufficiently small diameter to enter the distal end of said sub-port tube and to pass therethrough to cause said nozzle connector to be received on said upstanding nozzle connector.

3. An aerosol delivery system, comprising:

an endotracheal tube having a sub-port and a distal end base outlet;

a sub-port tube passing through said sub-port into an interior portion of said endotracheal tube;

said sub-port tube having a passageway and an atomizer nozzle disposed at its distal end, wherein said atomizer nozzle and said endotracheal tube are integrally connected to one another at about said distal end base outlet; and a canister for delivering fluid under pressure and having connected thereto a delivery conduit;

wherein said delivery conduit terminates at its distal end in an atomizer connector, and wherein said delivery conduit is configured to pass within said sub-port tube passageway a sufficient distance to enable said atomizer connector to lockingly engage said atomizer nozzle to form a fluid path from said canister to said atomizer nozzle;

whereby delivery of fluid under pressure from said canister flows within said delivery conduit to said atomizer nozzle to spray an aerosol mist outwardly from said base outlet.

4. The patient care device according to claim 3, further comprising a removable plug for sealing the proximal end of said sub-port tube whenever said delivery conduit is not disposed within said sub-port tube.

5. The patient care device according to claim 3, further comprising:

a canister for holding a medicating fluid under pressure, said canister being adapted to be connected to said delivery conduit.

6. The patient care device according to claim 5, wherein said canister has a thumb lever for causing a predetermined dose of said medicated fluid to be released from said canister whenever said thumb lever is actuated.

7. An aerosol delivery system, according to claim 3, wherein said canister includes a thumb lever for actuating the delivery of a sufficient amount of the medication fluid under pressure to facilitate medicating a patient.

8. An aerosol delivery system, according to claim 7, wherein said sufficient amount of the medication fluid under pressure is a predetermined dosage amount.

9. A patient care device, comprising:

air delivery tube means for facilitating ventilating a patient, said air delivery tube means having a proximal end opening, a distal end opening and a sub-port opening;

medication delivery tube means having a proximal end and a distal end, said medication delivery tube means extending through said sub-port opening and being attached to said air delivery tube means at about its distal end opening;

fluid atomizing means disposed within said medication delivery tube means, said fluid atomizing means being partially attached to said medication delivery tube means at about its distal end and partially attached to said air delivery tube means at about its distal end opening; and said fluid atomizing means having fluid delivery seat means for receiving therein nozzle connector means to facilitate medicating the patient, said nozzle connector means being disposed at a distal end of delivery conduit means having a sufficiently small diameter to enter the distal end of said medication delivery tube means and to pass therethrough to cause said nozzle connector means to be received within said fluid delivery seat means.

10. A medication delivery device, comprising:

a canister of medication fluid under pressure;

an elongated medication delivery tube adapted to be connected in fluid communication with said canister, said medication delivery tube having a sufficient small diameter to be received within a sub-port tube extending out from an endotracheal tube and being attached at its distal end to a distal end opening of said endotracheal tube; and a nozzle connector disposed within said medication delivery tube at about its distal end, said nozzle connector being adapted to be received in a fluid delivery seat of an atomizer nozzle disposed at about said distal end opening of said endotracheal tube.

11. A patient care device, comprising:

an endotracheal tube having a sub-port opening;

a sub-port tube extending through said sub-port opening and being attached to said endotracheal tube;

an atomizer nozzle having an upstanding nozzle connector disposed at a distal end of said sub-port tube and being connected to said endotracheal tube;

a delivery conduit having an atomizer connector disposed at its distal end and having a sufficient length to pass within said sub-port tube to lockingly engage said upstanding nozzle to facilitate causing an aerosol mist to be dispensed outwardly from said endotracheal tube.

12. The patient care device according to claim 11, wherein said delivery conduit is adapted to be connected to a canister for delivering fluid under pressure to said atomizer connector.

13. A method of medicating a ventilated patient, comprising the steps of:

inserting an endotracheal tube into the airway passage of the patient, said endotracheal tube having:
a sub-port opening;
a sub-port tube extending through said sub-port opening and being attached to said endotracheal tube; and
an atomizer nozzle having an upstanding nozzle connector disposed at a distal end of said sub-port tube and being connected to said endotracheal tube;

passing a delivery conduit having an atomizer connector disposed at its distal end and having a sufficient length to pass within said sub-port tube to lockingly engage said upstanding nozzle connector to facilitate causing an aerosol mist to be dispensed outwardly from said endotracheal tube;

attaching a proximal end of said delivery conduit to a canister of medicated fluid under pressure; and releasing a sufficient amount of the medicated fluid under pressure from said canister for delivery to the lungs of the ventilated patient through said atomizer nozzle.

14. In combination, with an endotracheal tube having a sub-port tube with an atomizer nozzle disposed at a distal end section thereof, said atomizer nozzle being connected to a distal end portion of said endotracheal tube and to a distal end portion of said sub-port tube to facilitate delivering an aerosol mist to the lung of a patient, a medication delivery device, comprising:

a canister having a medication and propellant disposed therein for further facilitating delivering the medication under pressure as the aerosol mist to the lung of the patient;

an elongated medication delivery tube attached to said canister at a proximal end section thereof;

said elongated medication delivery tube having a sufficient length to engage said atomizer nozzle disposed at the distal end portion of said endotracheal tube and a sufficiently small diameter to pass through said sub-port tube to engage said atomizer nozzle disposed at the distal end portion of said sub-port tube; and said elongated medication delivery tube further having an atomizer nozzle connector disposed at a distal end section thereof, said atomizer nozzle connector being adapted to lockingly engage a seat disposed at a proximal end portion of said atomizer nozzle to form a fluid tight seal therewith to further facilitate delivering the medication under pressure as an aerosol mist to the lungs of, a patient.

15. The combination according to claim 14, wherein said sub-port tube is partially disposed within an interior portion of said endotracheal tube and partially disposed outside of said interior portion of said endotracheal tube to facilitate delivering an aerosol mist to the lung of a patient, a medication delivery device.

16. A patient care device, comprising:

an endotracheal tube having a sub-port tube with an atomizer nozzle disposed at a distal end section thereof, said atomizer nozzle being integrally connected to a distal end portion of said endotracheal tube and integrally connected to a distal end portion of said sub-port tube to facilitate securing said atomizer nozzle within the patient care device; and said atomizer nozzle having a seat disposed at a proximal end portion thereof, said seat being adapted to lockingly engage an atomizer nozzle connector disposed at a distal end section of an elongated medication delivery tube to form a fluid tight seal to facilitate delivering medication under pressure as an aerosol mist to the lungs of a patient.

* * * * *